(12) United States Patent
Brocker et al.

(10) Patent No.: US 8,727,754 B2
(45) Date of Patent: May 20, 2014

(54) METHOD AND DEVICE FOR PRODUCING SOFT CAPSULES

(75) Inventors: Erich Brocker, Kirchberg (CH); Alois Peter, Wil (CH); Georg Sydow, Constance (DE)

(73) Assignee: Swiss Caps Rechte und Lizenzen AG, Kirchberg (CH)

( * ) Notice: Subject to any disclaimer, the term of this patent is extended or adjusted under 35 U.S.C. 154(b) by 69 days.

(21) Appl. No.: 13/258,809

(22) PCT Filed: Mar. 24, 2010

(86) PCT No.: PCT/EP2010/053824
§ 371 (c)(1),
(2), (4) Date: Dec. 6, 2011

(87) PCT Pub. No.: WO2010/108948
PCT Pub. Date: Sep. 30, 2010

(65) Prior Publication Data
US 2012/0128765 A1    May 24, 2012

(30) Foreign Application Priority Data
Mar. 26, 2009   (EP) ..................................... 09156266

(51) Int. Cl.
*B29C 41/00* (2006.01)
*B65B 3/00* (2006.01)
*B65B 3/08* (2006.01)

(52) U.S. Cl.
USPC .............. 425/5; 425/116; 425/132; 425/375; 425/464; 425/804

(58) Field of Classification Search
USPC ............. 425/116, 122, 123, 237, 804, 5, 132, 425/375, 464; 53/454, 560
See application file for complete search history.

(56) References Cited

U.S. PATENT DOCUMENTS

| | | | |
|---|---|---|---|
| 3,032,950 A * | 5/1962 | Oddo et al. | 425/5 |
| 4,408,641 A * | 10/1983 | Yamamoto et al. | 141/82 |
| 4,447,464 A | 5/1984 | Schwartz et al. | |
| 5,897,910 A | 4/1999 | Rosenberg et al. | |
| 6,402,496 B2 * | 6/2002 | Ishikawa et al. | 425/237 |

(Continued)

FOREIGN PATENT DOCUMENTS

| | | |
|---|---|---|
| EP | 0 227 060 A2 | 7/1987 |
| EP | 0 240 906 A2 | 10/1987 |

(Continued)

*Primary Examiner* — Joseph S Del Sole
*Assistant Examiner* — Thukhanh Nguyen
(74) *Attorney, Agent, or Firm* — Nath, Goldberg & Meyer; Jerald L. Meyer; Lakshmi Rajan

(57) ABSTRACT

The claimed subject matter relates to a rotary die device for producing soft capsules, comprising a capsule forming unit for forming a soft-capsule shell and a dosing unit for feeding a filling material into the capsule forming unit, characterized in that the dosing unit comprises a conveying apparatus of viscous melts and a portioner, wherein the portioner is connected at an end thereof to the conveying apparatus of viscous melts and is arranged in a filling wedge with a section in such a way that filling material from the portioner reaches the location of the capsule filling directly or by means of one or more channels having a length of at most 30 mm. Using said device, high-viscosity filling materials can be filled and thus novel soft capsules can be made accessible.

16 Claims, 7 Drawing Sheets

(56) References Cited

U.S. PATENT DOCUMENTS 6,569,363 B1 * 5/2003 Schurig et al. .............. 425/133.5
6,729,867 B2 * 5/2004 Peter et al. .................... 425/462
6,935,090 B2 * 8/2005 Stolz .............................. 53/454

FOREIGN PATENT DOCUMENTS

| EP | 1 216 680 A1 | 6/2002 |
| WO | 95/17153 A1 | 6/1995 |
| WO | 00/28942 A1 | 5/2000 |

* cited by examiner

METHOD AND DEVICE FOR PRODUCING SOFT CAPSULES

This is a National Phase Application filed under 35 U.S.C. §371 as a national stage of PCT/EP2010/053824, filed on Mar. 24, 2010, an application claiming the benefit under 35 U.S.C. §119 of European Application No. 09156266.0, filed on Mar. 26, 2009, the content of each of which is hereby incorporated by reference in its entirety.

The invention relates to a method for producing soft capsules. The invention also relates to a device for producing soft capsules and to a soft capsule containing a pharmacologically or physiologically active substance.

Soft capsules are nowadays usually produced by the rotary die method, which was described for the first time in U.S. Pat. No. 2,288,327. In this method, two bands of film, for example of aqueous gelatin solution, are guided over counter-rotating forming rolls and fused to each other. On their surface, these forming rolls have recesses (cavities), which are encircled by flanges. The two bands are suitably heated to below the melting point and fused to each other under the force of the flanges. At the same time, shaped articles in the form of soft capsules are severed from the bands by being pinched off. During the fusing of the bands, the capsules thereby forming are dosed with filling material through fine channels in the filling wedge. The principle of rotary die encapsulation is described, for example, in Fahrig/Hofer, Die Kapsel [the capsule], Stuttgart, 1983, page 70 et seq. A method and a device for producing soft capsules using starch-containing, melt-processed bands of film is described, for example, in EP 1 103 254.

The dosing of the filling material is performed with the aid of precision dosing pumps (piston-type dosing pumps), which are in the same generic category as reciprocating displacement machines. The metered volume of fluid is thereby brought up to the capsule halves on both sides through the filling wedge in a number of pulses, depending on the size of the volume by way of individual lines for each capsule of 30 to 70 cm in length. In this case, both the principle of half-dosing into each of the two capsule halves (Y-shaped duct) and single-channel conductance (I-shaped duct) up to the tip of the filling wedge (buttonhole segment) are customary. The capsules created are in this case made to bulge to the extent to which a pumping surge forces filling material into the capsule cups. Although the principle was described as long ago as 1935, the design of the pumps and of the filling wedge has remained substantially unchanged to the present day and is still in use.

A method for producing enclosed tablets that is not comparable to the rotary die principle is described in U.S. Pat. No. 5,897,910. In this case, two bands of film are introduced between two calendering rolls, the tablet material to be enclosed being introduced between the two films in liquid form.

EP 2 042 165 has described a method by which molten compositions can be encapsulated as filling material by using melt-processed enclosing material.

However, it is generally not possible by this prior art to encapsulate filling materials with a viscosity in excess of about 5000 mPa·s. EP 2 042 165 also preferably uses a conventional rotary die device in which the piston-type dosing pump with which the dosing of the filling material is carried out is arranged at a not inconsiderable distance (generally about 50 cm) from the actual location of the capsule filling in the filling wedge and the dosed filling material is conducted over this distance through fine channels in the filling wedge. Highly viscous filling materials of a strongly temperature-dependent viscosity cannot be filled in this way, since they cannot be satisfactorily transported through the fine channels, or solidify there. According to the prior art, lowering the viscosity by increasing the temperature of the filling material is also only feasible to a restricted extent, since the temperature of the filling material must lie below the sealing temperature of the enclosing bands, which in the case of gelatin solutions is at approximately 40° C., for starch/carrageenan solutions is at about 60° C.

In the production of molten filling compositions that contain one or more active substances (here API=active pharmaceutical ingredient, which should also be understood as meaning, for example, cosmetic substances or nutrients) it has been found that the conventional preparation of a melt generally also gives rise to problems of stability. While the conventional preparation of an API-containing matrix allows it to be filled into soft capsules over a time period of several hours at temperatures up to 40° C. without any appreciable losses of API through thermal, or thermal-oxidative, destruction, at temperatures above 100° C. it is no longer possible to ensure that the filling material can be stored without undesirable consequences.

It is therefore an object of the present invention to provide a method of the type mentioned at the beginning by which soft capsules can be charged with high-melting or viscous filling materials by means of the rotary die principle. It is also intended to provide a device suitable for this which can be produced at low cost and can be easily maintained. It is at the same time intended that the highly viscous melts can be dosed as precisely as possible.

This object is achieved with regard to the method by a method having the features described herein. Unlike in the case of the conventional piston-type dosing pumps, according to the invention the delivery means produces at least one continuous stream of filling material, preferably free from pressure fluctuations. This stream is divided into individual portions by a portioner arranged separately from the delivery means, preferably within the filling wedge, before said portions reach the capsule filling location.

The basic principle of the present invention is consequently that the dosing of the filling material does not take place as before spatially separate from the actual capsule filling location in the filling wedge but directly at this location. This dispenses with the troublesome transportation of the highly viscous filling material through relatively long fine channels.

Particularly advantageously, the filling material is prepared in the delivery means to form a viscous melt with a temperature of 51° to 200° C. The delivery means consequently performs a dual function as a pump and as a melting device.

Advantageously, the delivery pressure and the delivery distance between the delivery means and the capsule filling location are dimensioned such that, after leaving the delivery means, the filling material reaches the capsule filling location within less than 30 minutes, preferably within less than 10 minutes and still more preferably within less than 3 minutes. It has surprisingly been found that this time window of a few minutes is entirely sufficient to keep very many APIs sufficiently stable in the filling material even at temperatures of 51° to 200° C.

It is also particularly advantageous if the stream of filling material is divided by the portioner into at least two partial streams, which lead to separate filling locations, the division being performed in such a phase-shifted manner that the final capsule filling is achieved at the partial streams one after the other and in each case the second partial stream is released before the first partial stream is interrupted. This mode of operation makes it possible for a delivery stream that is free from pressure fluctuations to be maintained between the delivery means and the portioner.

It has been possible to achieve advantageous results when the individual portions of the stream of filling material are conducted between the portioner and the capsule filling location over a distance of 0 to at most 50 mm, preferably at most 30 mm. At the aforementioned high temperatures, these distances are sufficient to prevent deposits on the channel walls or even clogging of these channels.

The filling material may first be melted as a mixture of matrix material and active substance and then intermediately stored in a solid, comminuted state. Subsequently, the ready-prepared filling material can be melted again and fed to the portioner by the delivery means, if need be also in very small batches. Consequently, a desired filling material can always be retrieved, without the active substance being impaired.

The delivery of the stream of filling material to the portioner is advantageously performed with a circulatory displacement delivery means. This may be a screw pump and preferably a melt extrusion device. Screw pumps have the advantage of pulsation-free delivery. However, gear pumps or vane pumps would also be conceivable, for example.

Further advantages can be achieved with the method if, when it is dosed at room temperature, that is to say at a temperature of 0° to 60° C., preferably of 0° to 50° C., the stream of filling material has a dynamic viscosity of more than 5000 mPa·s. If, on the other hand, the temperature is more than 50° C., the viscosity should be more than 10 mPa·s, more preferably more than 1000 mPa·s and still more preferably more than 5000 mPa·s.

With regard to the device, the object is achieved according to the invention by a device having the features described herein. It is in this case particularly preferable to arrange the portioner within the filling wedge. Within the filling wedge means between the two convex wedge surfaces and as close as possible to the surface thereof. However, in certain cases and depending on the dimensioning of the filling wedge, it will also be conceivable to place the portioner outside the filling wedge, that is to say for example at an extreme end or on the upper side of the filling wedge.

As already mentioned, the delivery means is advantageously a circulatory displacement delivery means, in particular a screw pump and preferably a melt extrusion device. Arranged on the surfaces of the filling wedge between the portioner and the capsule filling location are distributing channels, the maximum length of which is 50 mm, but preferably merely 30 mm.

To prevent pressure surges, the stream of filling material can be divided at the portioner into at least two partial streams, which can be directed to separate filling locations directly or by way of separate distributing channels, it being possible for the partial streams to be achieved phase-shifted one after the other. For this purpose, opening cross sections for each partial stream can be exposed and closed again one after the other on the basis of two sinusoidally superposed curves.

The portioner may have at least one dosing hollow shaft, which is rotatably mounted in the filling wedge and has discharge openings, which in at least one rotary angle position coincide with an opening or with a channel in the filling wedge. Such a dosing hollow shaft can be accommodated in a space-saving manner and close to the surfaces of the filling wedge. The dosing hollow shaft can penetrate from the two extreme ends or from the surface of the filling wedge into the filling wedge in any desired relative position. However, it is particularly advantageous if the dosing hollow shaft is mounted parallel to the axes of rotation of the forming rolls and if each discharge opening can be connected either to a channel leading to the wedge surfaces or to a channel leading to the wedge tip of the filling wedge. The use of a number of dosing hollow shafts, for example on each longitudinal side of the filling wedge, would also be conceivable. If the dosing hollow shafts counter-rotate, a frictionally induced torque on the filling wedge could be neutralized.

The portioner could, however, also have at least one dosing slide, which is mounted linearly displaceably in the filling wedge and with which feed channels for the filling material can be exposed and closed in a cyclical manner. Such a dosing slide could also penetrate into the filling wedge from any side of the filling wedge, with the exception of the wedge surfaces. Here, too, the use of a number of dosing slides or pairs of dosing slides would be conceivable. Advantageously, the at least one dosing slide is mounted perpendicularly to a plane running through the two axes of rotation of the forming rolls. This has the advantage that no torque is exerted on the floating filling wedge and that more space is available for the mounting over the filling wedge.

However, the dosing slide could also be formed as a dosing tube by way of which filling material can be fed. The function of the dosing tube would consequently be comparable to that of the dosing hollow shaft, but with the movement not being rotational but linear.

Finally, it would also be conceivable for the portioner to be configured as a valve with at least one valve needle, which interacts with a valve seat in the filling wedge. Thus, depending on the dimensioning of the valve seat, the division of the stream of delivered material could take place with very small valve lifts.

According to the present invention, a highly viscous filling material should be understood as meaning a material which, when it is dosed into soft capsules, has a viscosity of more than 5000 mPa·s. Since a transition from solid to liquid (melt) or a reduction in the viscosity generally takes place when there is an increase in the temperature, this limit value of 5000 mPa·s should be understood as being at the lowest temperature that is technically possible for dosing and encapsulation.

According to the present invention, the filling material is produced in the form of a melt in a device for delivering viscous melts. Subsequently, the molten filling material is conducted through a portioner at least partially arranged directly in the filling wedge. This portioner preferably comprises a rotatable dosing shaft, which will be described in more detail below.

According to the present invention, a device for delivering viscous melts is preferably understood as meaning a melt extrusion device or a melt pump (single- or twin-screw extruder). The portioner is connected at one end directly to the device for delivering viscous melts and is installed movably in the filling wedge.

In another embodiment according to the present invention, the portioner may take the form of a slide, the dosing slide being connected at one end to the melt extrusion device and having on a portion, located in a filling wedge, at least one perforation, which can be opened and closed by pushing a closure unit forward and back. The arrangements shown below for a dosing shaft can also be used for such a slide, with the difference that the dosing channels are not released with the aid of a rotational movement, but with the aid of a movement forward and back.

In a further embodiment according to the present invention, the portioner may comprise a dosing channel, which is connected at one end to the melt extrusion device and has on one portion, located in a filling wedge, at least one perforation, the dosing channel being arranged immovably in the filling wedge and it being possible for the at least one perforation to be opened and closed by means of a valve. Preferably, the valves may be controlled by means of a camshaft.

The dosing shaft shown in more detail below is preferred in terms of its structural design, since, by selection of the materials, for example steel coated with PTFE (polytetrafluoroethylene), hardened steel or ceramic, it can be made to fit exactly and can be operated with or without lubricants and sealants. Furthermore, the dosing shaft can be rotated/pivoted in a cyclical manner or rotated continuously and the speed of movement can be easily adapted to the viscosity, capsule size, filling channel diameters, etc.

One portion of the dosing shaft is located in the filling wedge and has perforations. These perforations (holes) connect the dosing shaft to recesses in the forming rolls either directly or by way of short channels.

The dosing shaft is arranged in the filling wedge in such a way that its portion having perforations is positioned directly at the actual capsule filling location or only a little way from it.

According to one embodiment of the present invention, between the portioner and the filling material outlet hole there is a dosing channel with a length of less than 50 mm, preferably less than 30 mm. Ideally, however, the portioner, preferably the dosing shaft, is the closure mechanism for the filling material hole directly, and there is no need for an actual filling material channel.

The highly viscous filling material is conducted without any problem by the comparatively thick dosing shaft into the filling wedge up to the actual capsule filling location. It is advantageous in particular that there can scarcely be any uncontrolled drop in pressure or temperature over this short distance.

A viscous composition can be metered through the perforations in the portioner, preferably the dosing shaft, into the recesses of the forming rolls when the perforations and recesses are connected to one another in a communicating manner. This is the case in a first position, in which either the perforations of the dosing shaft open exactly into the recesses of the forming rolls, or in which the perforations of the dosing shaft are arranged in register with openings of channels provided in the filling wedge, the outlet openings of the channels for their part being positioned in register with the recesses in the forming rolls.

As long as this communicative connection exists, the filling material is dosed into the recesses of the forming rolls. This communicative connection is discontinued by the dosing shaft being turned out of the first position, so that the perforations of the dosing shaft no longer open directly into the recesses of the forming roll or into the connecting channels in the filling wedge. Consequently, turning the dosing shaft at a certain speed can achieve the effect that an exact dosed amount of filling material passes through the perforations into the recesses of the forming rolls.

In this way, a completely different dosing principle is used according to the present invention than was previously customary in the prior art with piston-type dosing pumps. The dose is no longer a volume that is metered in advance by piston volumes and issues into the capsule as a result of repeated successive delivery of a hydrostatic "column", but a volume that issues into the capsule as a result of defined openings in dependence on time, temperature, viscosity and pressure.

A dosing shaft according to the invention preferably has at least the length of a filling material wedge, that is to say 7.5 inches, 10 inches etc., a diameter of 2-5 cm and a wall thickness of 1-5 mm. The bores (perforations) for the issuing of the viscous filling material may be of a round or slit-like type.

The dosing may also be achieved by corresponding turning of the forming rolls. However, it is preferable to achieve the shearing off of the stream of filling material by turning of the dosing shaft, since then this task does not have to be undertaken by the sensitive bands of film and no filling material can get between the filling wedge and the band.

A dosing slide, that is to say a hollow shaped part which is of a round rod-shaped or flat cuboidal or more complexly shaped form and is filled with filling material, may be used very similarly, likewise having outlet openings, but the opening and closing mechanism thereof does not operate by turning or rocking but by pushing forward and back.

Similarly, perforations (holes) arranged in a fixed dosing channel (for example a dosing cylinder) may be opened and closed by valves for the passing through of viscous filling material.

According to a preferred embodiment of the present invention, the dosing shaft has on its portion located in the filling wedge at least two perforations, which in a first position lead directly into recesses of two forming rolls and in a second position are separated from the recesses in the forming rolls, it being possible for the first position to be transformed into the second position by turning of either the dosing shaft or the forming rolls. The first variant (turning of the dosing shaft) is preferred, since then, as described above, the shearing off of the stream of filling material is achieved by turning of the dosing shaft.

According to further embodiments of the present invention, in the filling wedge there is at least one channel, which in a first position connects a perforation of the dosing shaft to recesses of the forming rolls in a manner allowing communication. This channel is short in comparison with the channels in the filling wedge to be found in the prior art. While in the prior art, as described, the filling material is dosed in a remote dosing pump, and subsequently has to be conducted to the actual filling location through fine channels of 1-3 mm in diameter over a distance of approximately 50 cm, the channels in the case of the present invention serve only for bridging the short distance between the perforations of the dosing shaft arranged within the filling wedge and the recesses in the forming roll. Even when highly viscous filling material is used, no problems such as solidification or clogging of the channels occur within this short distance.

The channels are preferably not longer than 30 mm, still more preferably not longer than 5 mm. The diameter of the filling channel is at least 1 mm, more preferably 2 mm, still more preferably $\frac{1}{3}$ of the capsule diameter, or $\frac{1}{3}$ of the cup width running past the filling hole.

According to the present embodiment, various configurations of the channel or channels are possible. For example, there may be a single channel, which in a first position connects a perforation of the dosing shaft to a cavity formed by two recesses of different forming rolls and can conduct filling material into this cavity (buttonhole filling).

According to another embodiment, in the filling wedge there is a channel of a Y-shaped form. In other words, starting from the end facing the perforation, in the dosing shaft the channel divides into two channels, which each lead to a recess of a forming roll. In this case, the recesses of the forming rolls are separately filled, so that during the subsequent fusing to form the final capsule, the filling material is already inside the capsule.

According to a further embodiment, a number of separate channels which can be sequentially connected to perforations of the dosing shaft and recesses in forming rolls are provided in the filling wedge. In this way, a cyclical dosing of the filling material is possible. Four separate channels located in pairs on the right and left of the dosing shaft are preferably provided here in the filling wedge, so that, in a first position, the two channels arranged further down in the filling wedge connect two perforations of the dosing shaft in a communicating manner to recesses of the forming rolls and, in a second position, the two channels arranged further up in the filling wedge connect two perforations of the dosing shaft in a communicating manner to recesses of the forming rolls, it being possible for the first position to be transformed into the second position by turning of the dosing shaft.

The number of perforations in the dosing shaft can be chosen as a matter of routine by a person skilled in the art to correspond to the conditions of the process. In a customary configuration according to the invention, the dosing shaft has four perforations. These perforations are preferably respectively spaced apart from one another by a quarter circle segment. In the case of the embodiment described above with a number of separate channels, preferably four, however, it may be advantageous to choose a smaller distance between every two neighboring perforations, for example an eighth circle segment. The distance from the next perforation then increases correspondingly (in the case of 4 perforations).

The perforations are arranged on the portion of the dosing shaft located in the filling wedge in such a way that they can be connected in a communicating manner to the recesses of the forming rolls directly or by way of channels in the filling wedge, and preferably have a diameter which corresponds to the diameter of the channel or channels in the filling wedge.

The dosing shaft may be installed in a customarily used filling wedge of a rotary die device. For this purpose, a bore which has a slightly greater diameter than the outside diameter of the dosing shaft should be created in the filling wedge, so that the dosing shaft can be turned frictionlessly within the filling wedge. In comparison with a conventional filling wedge, furthermore, the otherwise customary long channel from the piston-type dosing pump (normally not present according to the invention) to the actual filling location is not required, and is therefore generally omitted. Instead, the at least one channel described above, which connects at least one perforation of the dosing shaft to recesses of the forming rolls, should be provided in the filling wedge.

According to one embodiment of the present invention, however, a conventional filling material feed by means of a separate piston-type dosing pump may be present in addition to the dosing device described here, in order that the rotary die device according to the invention can also be operated in a conventional way if required.

According to the invention, the dosing shaft is led through the filling wedge. As described above, one end of the dosing shaft is connected to a device for delivering viscous melts. The other end of the dosing shaft, which leaves the filling wedge on the side facing away from the device delivering viscous melts, is connected to a motor, which can set the dosing shaft in a rotational movement. Any customary motor which can impart a continuous or oscillating movement to the dosing shaft may be used here.

The rotational speed or oscillating speed of the dosing shaft may be freely chosen by a person skilled in the art to correspond to desired process conditions and is synchronized with the speed with which the capsule cups are offered in such a way that filling begins shortly after positioning of the filling hole within the periphery of the capsule cup and ends shortly before positioning of the filling hole in front of the opposite periphery of the capsule cup.

According to the invention, the filling wedge with dosing shaft described above, or the dosing slide, or the dosing channel with valves is installed together with the melt extrusion device in a conventional rotary die device. Rotary die devices and the rotary die process are generally known and are described, for example, in EP-1 103 254 A1. Reference is expressly made to the corresponding disclosure of EP-1 103 254 A1.

Any conventional melt extrusion device may be used for the preparation of the filling material. These devices are known to a person skilled in the art and do not have to be explained here in detail.

In order to compensate for any pressure fluctuations in the dosing shaft caused by the operation of the device for delivering viscous melts, according to a preferred embodiment of the invention a pump with a differential pressure regulating unit may be provided on the dosing shaft, for example between the device for delivering viscous melts and the dosing shaft.

The present invention succeeds in producing soft capsules with meltable filling material by means of the rotary die technique with the least possible thermal impairment and in improving the dosing technology, especially in cases of high viscosity of the filling material.

In order to make use of this effect for the production of capsules with high-melting filling materials, some basic principles should be followed and put into practice with the device according to the invention:

continuous production of the filling material and filling of the soft capsules without any time delays (no batch mode);

dosing of API, mixing with the filling material matrix and melting to form a homogeneous composition or remelting of a cooled-down homogeneous melt directly before dosing and encapsulation ("melt-on-demand");

exact dosing with scarcely any pressure fluctuations;

gentle shearing off of the portioned dose from the highly viscous "strand" without involvement of/contact with the enclosing composition;

monitoring of/compensation for heat losses;

rapid cooling after forming.

The present invention consequently also relates to a method for producing soft capsules, comprising the steps of
a) preparing a filling material in a device for delivering viscous melts at a temperature in the range from 51° C. to 200° C.,
b) continuously feeding the filling material into the interior of a capsule formed by two bands of film by means of forming rolls,
characterized in that steps a) and b) are carried out in a device described above within a time period of less than 30 minutes, preferably less than 10 minutes and still more preferably less than 3 minutes.

With the device according to the present invention, these principles can be followed at the same time. The filling wedge described above, designed for dosing with high viscosities, allows a direct coupling of feeds of filling composition from melt extrusion devices under elevated pressure and elevated temperature. Consequently, with the device according to the invention there is minimal cooling while maintaining a uniform pressure. The filling material is offered locally and at the time it is required.

According to the present invention, the introduction of the filling material in the capsule forming step (for example of the rotary die method) is likewise performed at elevated temperature, which is at least so high that the molten filling material flows sufficiently and can be dosed, but is 10-150° C. lower, preferably 20-50° C. lower, then the sealing/fusing temperature of the thermoplastic enclosing films.

It has been found that the conventional making up of filling material in batch mode, that is to say producing a relatively large amount of filling material in one batch, preferably in a tank, means that the API contained therein is subjected to considerable thermal loading, in particular since it generally takes several hours to days after production before a composition undergoes filling, and the entire filling material must be kept in a flowable state at elevated temperature.

The stability is generally increasingly impaired by time, temperature (Arrhenius equation), crystallinity (or molecularly disperse distribution (solution)) and presence of other reactive substances (substance mixtures).

The production of such compositions and the problems of thermal degradation have already been published. However, filling into shaped articles of the core-shell kind such as soft capsules is novel. It has surprisingly been found that, for most common pharmaceutical, "nutritional" active substances (vitamins, mineral supplements, etc.) (here referred to generally as APIs), the temperature-time profile that is obtained from processing in an extruder and correspondingly rapid dosing in rotary die encapsulation at relatively high temperatures has no adverse effects. This is particularly so if a) the individual raw material components have been melted under a vacuum or shielding gas;
b) mixing of the components is performed at the last moment before introduction into the capsule (particularly suitable is a continuous melting, mixing and degassing process such as in a single- or twin-screw extruder);
c) the dosing into the capsule halves is performed as soon as possible after melting, which according to the invention is performed by a novel way of conducting composition and dosing;
d) there is rapid cooling of the capsule produced;
e) the thermoplastic enclosing material is tolerant to softening and shock cooling cycles;
f) attention is paid to water vapor pressure or water concentration during the operations of encapsulation and cooling (low water content).

Although the present invention is designed for the use of highly viscous filling materials, it is also very well possible with the device according to the invention that low-viscosity filling materials can be filled satisfactorily, since delivery and dosing are performed isobarically, there is no resonating hydrostatic volume and dosing takes place directly at the capsule without any dead volume.

According to the invention, the filling material is preferably produced directly before the encapsulation continuously from the corresponding starting components by melting and mixing. Preferably, at least one active substance in solid form is continuously dosed together with a suitable filling material matrix in a twin-screw extruder, mixed and melted together and ideally—dependent on the components chosen—dissolved. A molecularly disperse melt is obtained.

"Molecularly disperse" is understood according to the present invention as meaning a solution or solution-like to colloidal distribution of the API, which is substantially free from macroscopically discernible concentrated accumulations of the API in crystalline or amorphous form. The molecularly disperse phase may be liquid (solution), semisolid (solid and liquid present together) or solid (glass or partially crystalline/crystalline).

The length (L) and the diameter (D) and also the configuration of the internal delivery screws of the device for delivering viscous melts can be chosen as a matter of routine by a person skilled in the art to correspond to the desired application conditions.

The same applies to the temperature profile, the pressure at the die, the dwell time and the delivery rate in the extruder. However, these variables are not quite independent from one another, so that it may prove to be advantageous for example to choose by means of a melt pump the delivery volume and pressure for offering into the dosing system to be different from the pressure of the extruder.

In a further variant according to the invention, the melt matrix may be formed into a strand, cooled, cut and intermediately stored as it is alone or as an API-containing melt.

In what is known as a "melt-on-demand system", as commercially available for example from Robatech, Muri, Switzerland or ITW Dynatec, 31 Volunteer Drive, Hendersonville, Tenn., it is logistically particularly advantageous that, in a further step, portions of the material can be quickly remelted in a controlled manner and without impairment and, by means of a melt pump, offered again with the pressures, temperatures and delivery rates desired for the capsule dosing system.

In a further embodiment, the API may be introduced in crystalline form into an already melted matrix if a further doser mixes in the API in the course of the twin-screw extrusion, or if the matrix mixture produced in a first extruder is kneaded in in a further extruder. In the case of this embodiment (single-screw, twin-screw), a person skilled in the art can choose the size and length (L/D) of the extruders as a matter of routine to correspond to the desired application conditions (substance, flow, temperature, viscosity, time). It is thus possible—if desired—also to ensure that the crystallinity of the API is retained. Particularly preferably, the active substance is added to the melt in a controlled grain size or microparticulate form (micronized, pelletized or coated).

In an embodiment for rapid melting and mixing operations and low-viscosity compositions, production in extruders may be followed not only by the dosing according to the invention but also by dosing directly by means of a conventional piston-type pump into a soft capsule with a thermoplastic enclosing shell.

In a particularly preferred embodiment, a melt pump with a differential pressure controller is arranged downstream of one or more extruders or melt-on-demand systems. This pump makes it possible for the melts to be delivered into the doser virtually free from pressure fluctuations. Such systems are commercially available, for example from Harrel Inc., East Norwalk, Conn., USA. Suitable melt pumps are also available, however, from Robatech, Muri, Switzerland; Kreyenborg, Münster, Germany; Witte, Uetersen, Germany or other manufacturers in the plastics industry.

The invention proposes a dosing system which can dose high-viscosity hot melts into capsule halves without any time delays and with direct connection to an extruder or melt pump. According to the invention, suitable for most APIs are temperatures below 150° C., preferably below 120° C., preferably below 90° C., and a processing time from dosing to introduction into the capsule of less than 30 minutes, more preferably less than 10 minutes, still more preferably less than 3 minutes.

A person skilled in the art will choose for these conditions the substance composition of a melt with the lowest viscosity. However, the arrangement according to the invention ensures a much greater latitude for the viscosity in comparison with the conventional technology of soft capsule production, including for the substance components that are used (monomers and polymers).

According to the invention, the capsule is preferably shock-cooled after production, in order to make the filling material glassy. This is preferably performed by cold gases (nitrogen, air, $CO_2$) or by a cold bath of liquids that are compatible with the enclosing shell.

The present invention succeeds in transferring the galenic advantages (in particular retardation and molecular disperibility) known from the production of melt-extruded dosing forms (for example Metrex) to core/shell structures, and consequently to completely and uniformly coated forms of administration, that is to say soft capsules. Thus, the advantages of the melt extrusion technique for the dosing of specific APIs can be combined with the advantages of completely enclosed forms of administration (encapsulation). In particular, the use of thermoformed films for shells of capsules enclosing filling materials produced by melt extrusion technology makes it possible for example also to use acrylates. This allows, for example, the forming of capsules with an enclosing shell of acrylates that are resistant to gastric juices and retarding of the filling material by acrylates or other polymers in one step.

However, it is also conceivable to use for the enclosing shell and for the filling material thermoplastics that have a particularly low water content, break up pH-dependently or can be broken down by digestive enzymes or generally enzymatically at a defined location.

The present invention allows soft capsules, comprising an enclosing shell and a filling material with at least one pharmacologically or physiologically active substance, to be produced in principle in such a way that the enclosing shell is made up of polymeric material which can be melt-processed by melt extrusion and has a sealing temperature of up to 250° C. and the molten filling material is filled at an elevated temperature between 50 and 180° C., but below the sealing temperature of the enclosing material, with viscosities of up to 100 000 mPa·s. The limits of the viscosity at the processing temperature are set in the downward direction exclusively by the tolerance of the melt extrusion devices (in the case of extruders, for example, the gap between the barrel and the screw) and in the upward direction by the relative time/pressure conditions that are available for the capsule filling.

The present invention overcomes a series of technological obstacles that the prior art has not been able to resolve:
Protection of the active substances from harmful heat during make-up/production;
Processing of high-viscosity melts;
Continuous forming and a single-stage process (by contrast with injection molding or calendering or forming followed by coating);
Adaptation of the processing temperatures of the enclosing shell and the filling composition such that the then possible acceptance of higher viscosities allows the filling material to be processed at a temperature at least 20° C. lower than the composition for the enclosing shell, so that optimum melting of the two enclosing bands is obtained, and consequently an enclosure of a consistent thickness;
Variable setting of the release behavior (resistance of the enclosing shell to gastric juices, immediate or retarded release of the active substance);
Avoidance of the recrystallization of the API or filling material matrix from glassy or partially crystalline systems;
Avoidance to a great extent of solvents (low molecular weight substances with high vapor pressure), unless the formulation of the filling material requires the presence of solvent on account of the solubilities of the API.

The following advantages over the prior art are obtained according to the present invention:
The soft capsule according to the invention is mechanically flexible and stable. The capsules are enclosed on all sides, cannot run out, and are API-free on the outer side of the enclosing shell;
The soft capsule filling materials according to the invention can be easily formulated in such a way that they are released in a retarded manner;
The mechanical/chemical properties of the enclosing shell of the soft capsule according to the invention can be easily adapted to different properties of the filling material or the climatic storing conditions;
The capsule shell may be formed from various thermoplastic materials, in particular also from polymers resistant to gastric juices. There is no need for an additional coating in the case of the soft capsules according to the invention;
Before and during the melt processing and forming and during the storage of the capsule, the capsule shell only contains at most as much water as the polymer material can take up by sorption from the store room humidity. The filling material compositions therefore scarcely undergo any change by water or plasticizer transfer. It is of course also possible to use a polymer which has been dried, or to which the necessary amounts of plasticizer or solvent or water for the plasticity or mechanical characteristics during use have been added;
It is possible to use not only filling material matrices that are based on polymers, but also those that are based on rapidly water-soluble small molecules which melt and solidify in a glassy, crystalline or partially crystalline form;
It is possible to eliminate the interaction of the enclosing shell and the filling material, since, with increasing solidity and increasing uniformity of the phases of the filling material, the exchange of plasticizer or other small molecules (diffusion) also decreases in particular;
The molecular dispersity of filling materials can be obtained with increasing solidity and increasing uniformity of the phases. The recrystallization of the active substance is prevented.

With the present invention, novel combinations of enclosing material and filling material that could not previously be realized for technical process-related reasons are possible. Since, with the device according to the invention, even high-viscosity filling materials at relatively high temperatures can be encapsulated, the use of other capsule materials is also possible.

The encapsulating material is made up of polymeric material which can be melt-processed by melt extrusion. For the purposes of the present invention, melt extrusion should be understood as meaning producing, deforming and fusing a thermoplastic composition at pressures of more than 1 bar (preferably more than 10 bar, still more preferably more than 100 bar) and temperatures of more than 60° C., or preferably more than 80° C., still more preferably more than 100° C.

In melt extrusion, a band of the corresponding material is formed, in that the material is brought into the form of a film through a slot die or with the aid of blowing methods at viscosities which do not allow processing using gravity (casting). In melt extrusion, therefore, the temperature and the pressure must necessarily be increased in comparison with ambient conditions (the temperature by at least 20-50° C. and the pressure to more than 10 or even more than 100 bar). Plasticizer and/or water and commonly used additives, such as for example lubricants, may be added to the melt-processable material. The melt extrusion may be carried out in a twin-screw extruder or single-screw extruder sufficiently well-known to a person skilled in the art.

According to the invention, the polymeric material which can be melt-processed by melt extrusion may be chosen, for example, from the group comprising polyvinyl pyrrolidone, cellulose ester and cellulose ether, polyvinyl alcohol, polyvinyl alcohol acetals, polyethylene glycol/polyvinyl alcohol graft polymer, polyacrylic acid (Carbopol), polyacrylate, polyoxyethylene (Polyox), polyoxypropylenes, starch, polylactic acid, polylactic acid-coglycolides, gelatin, carrageenan, casein, gluten and mixtures thereof.

Examples of materials that are suitable according to the invention are the starch-containing compositions disclosed in EP 1 103 254 A1 and the enclosing materials disclosed in EP 1 586 436 A1, enclosing materials based on PVACL being preferred in the latter case.

According to the invention, it is also possible to use the thermoplastic polymers described in EP-1 586 436 A1, which are chosen from the group comprising polyvinyl alcohol, cellulose ether, polycaprolactone, polyamides, polyacrylic acid, polyvinyl pyrrolidone, polylactic acid or polyvinyl alcohol acetals (PVACL), derivatives or mixtures of the same. Reference is expressly made to the corresponding disclosure of EP-1 586 436 A1.

Furthermore, all melt-processable polymers with a sufficient flowing and sealing temperature between 80 and about 250° C., and also sufficient strength and elongation near the sealing temperature and sufficient flexibility and impact resistance can be used as enclosing material, irrespective of whether or not they are water-soluble.

In addition to the groups enumerated above, or individual polymers mentioned, the following may be of interest for oral administration to humans (without being an exhaustive list): hydroxypropyl cellulose (HPC), hydroxypropyl methylcellulose (HPMC), ethylcellulose (EC), cellulose acetate phthalate (CAP), hydroxypropyl methylcellulose phthalate (HPMCP), hydroxypropyl methylcellulose acetate succinate (HPMCAS, Aqoat), sodium carboxy methylcellulose (CMC), polyvinylpyrrolidone (PVP), polyvinylpyrrolidone/vinyl acetate copolymer (Kollidon VA), polyvinyl alcohol/polyethylene glycol graft copolymer (Kollicoat IR), Carbopol (polycarbophil), methacrylic acid copolymer (Eudragit), methacrylic acid/ethyl acrylate copolymer (Eudragit), aminoalkyl methacrylate copolymers (Eudragit), polyethylene glycol, Polyox, maize protein (zein), wheat protein, and soya protein (gluten).

According to the invention, the enclosing shell preferably consists of a thermoplastic polymer which is water-soluble at 37° C. for oral administration in the pharmaceutical or food sector.

Furthermore, according to the invention the enclosing shell preferably consists of polymers which are resistant to gastric juices or dissolve pH-dependently.

From these materials, films which can be processed into soft capsules in customary soft capsule production processes, such as for example the rotary die process, can be created by melt extrusion. This provides significant advantages over the prior art of soft capsules, where the formed soft capsule has to be coated with a functional polymer in a second step to achieve certain properties of the enclosing shell, such as resistance to gastric juices.

By contrast with the enclosing material, which has to meet certain minimum requirements in terms of mechanical properties at the processing temperature (feeding, elongation during filling, sealing), all that has to be ensured for the molten filling material composition is that the temperature of the composition lies below the processing temperature of the band when it is introduced into the half of the soft capsule. The other mechanical characteristics, with the exception of maximum viscosity, are not of any great importance.

The formulation of the filling material is therefore chosen such that a maximum viscosity for the dosing is not exceeded at the processing temperature of the band. For this purpose it is sufficient to choose suitable substances (polymers, polymer/monomer mixtures) and to choose the right chain lengths of a polymer.

For use as an oral form of administration in the area of nutrition or pharmacy, it is intended that the filling materials according to the invention should exhibit sufficient potential bioavailability on contact with water. "Potentially sufficient bioavailability" is understood as meaning an immediate or delayed molecularly disperse offering of the API in the gastrointestinal tract that is adapted to the pharmacological action and the physiological conditions. With good water solubility of the substance, it is intended that at least 80% of the API should be dissolved in the required time in the liquids of the gastrointestinal tract, which can be measured as a simulation with what is known as the release. For APIs that are poorly water-soluble or lipophilic and cannot be mixed with water, this is understood as meaning the emulsification of at least 80% of the API in the form of droplets, colloidal or other complicated structures with a surface area of at least 1000 times the original "capsule filling material surface area".

The transition from the "solid" state into the "plastic" or "liquid" state can be described in the case of low molecular weight and crystallizing substances by what is known as the melting point (mp). The melting temperature refers to the temperature at which a substance melts, that is to say goes over from the solid state of aggregation into the liquid state of aggregation. The melting temperature is dependent on the substance but, by contrast with the boiling temperature, is only dependent very little on the pressure (melting pressure). The melting temperature and the melting pressure are together referred to as the melting point, this describing the state of a pure substance and being part of the melting curve in the phase diagram of the substance. For pure substances, the melting point is identical to the freezing point and remains constant during the entire melting process.

For polymers, amorphous or glassy substances, the transition temperature or glass temperature is characteristic. The glass transition temperature or softening temperature (Tg) is the temperature at which a glass has the greatest change in deformability. This glass transition, as it is known, separates the lower brittle energy-elastic range (=glass range) from the upper soft entropy-elastic range (=rubber-elastic range). The transition into the flowing range of the amorphous plastic is smooth. Partially crystalline plastics have both a glass transition temperature, below which the amorphous phase 'freezes' (accompanied by embrittlement), and a melting temperature, at which the crystalline phase breaks up. The melting temperature clearly separates the entropy-elastic range from the flowing range. By contrast with this, crystalline plastics only have a melting temperature.

For blends and mixtures of all kinds, the melt flow index is suitable, for example, for describing the behavior of the viscosity in dependence on the temperature. Measuring the melt flow index is a technological test method for the rapid, qualitative determination of the flow properties of thermoplastic molding compositions. The melt flow index represents a measure of the flowability of the polymer melt at the chosen temperature and is primarily determined by the average molecular weight. The melt flow index (MFI) in g/10 min at temperature T is defined here as the mass of composition that is forced through a standardized die within a time period of 10 minutes under a fixed piston force and at a specific temperature T of the composition.

By contrast with the prior art, it has previously only been possible to introduce molecularly disperse filling material systems into capsules if they were still pumpable at the temperature at which the enclosing material seals. The increase in the sealing temperature of the enclosing materials, caused by the newly possible melt processing of the enclosing polymers into films, makes it possible to offer higher-melting (>51° C.) and higher-viscosity compositions. A person skilled in the art is given much more latitude in the selection of substances for the formulation of a filling material system containing at least one API. The dependence on temperature and viscosity allows the development of the filling composition to be based on one OR the other parameter.

The following may be mentioned as soft capsules produced according to the invention, without implying any restriction:

EXAMPLE 1

| | |
|---|---|
| Gelucire 50/13 (Lauroyl macrogolglycerides, mp 44° C.) | 262.5 mg |
| Lutrol F127 (Pluronic F127, poloxamer 407, mp 57° C.) | 262.5 mg |
| Diclofenac sodium (mp 284° C.) | 75.0 mg |

The viscous molten suspension was filled into soft capsules with an enclosing shell of PVA/starch at an extruder die temperature of 75° C. and with a viscosity of 5000 mPa·s; capsules with delayed release (retarded) with a white solid content were obtained. The particle size distribution of the diclofenac remained virtually unchanged.

EXAMPLE 2

| | |
|---|---|
| Ascorbic acid (mp/dec. 190° C.) | 180 mg |
| Klucel EF (hydroxypropyl cellulose) (softening temp. >130° C.) | 180 mg |
| Sorbitol (Sorbidex P16616/Cargill) (mp 166-168° C.) | 50 mg |
| Triethyl citrate | 40 mg |

The mixture allowed itself to be processed at 130-140° C. into a doughy, white opaque composition, which exhibited quite a high viscosity (about 100 000 mPa·s), and was filled into 7.5 minims soft capsules with an enclosing shell of PVA/starch at an extruder die temperature of 110° C. Capsules with delayed release (retarded) were obtained.

EXAMPLE 3

| | |
|---|---|
| Ibuprofen (mp 74-77° C.) | 210 mg |
| Kollidon K30 (polyvinyl pyrrolidone) (softening temp. >150° C.) | 260 mg |
| Isomalt (mp 145-150° C.) | 47 mg |
| Water | 3 mg |

In the extruder, the above components were melted at a maximum of 120° C. to form a clear homogeneous viscous melt of about 20 000 to 50 000 mPa·s (about 110° C.) and filled into 10 minims oval starch capsules at a die temperature of 90° C. About 80% of ibuprofen was released in 45 minutes (900 ml of water, 37° C., paddle 100 rpm).

The present invention is explained below on the basis of preferred, non-restrictive embodiments and drawings, in which.

Figure 2:
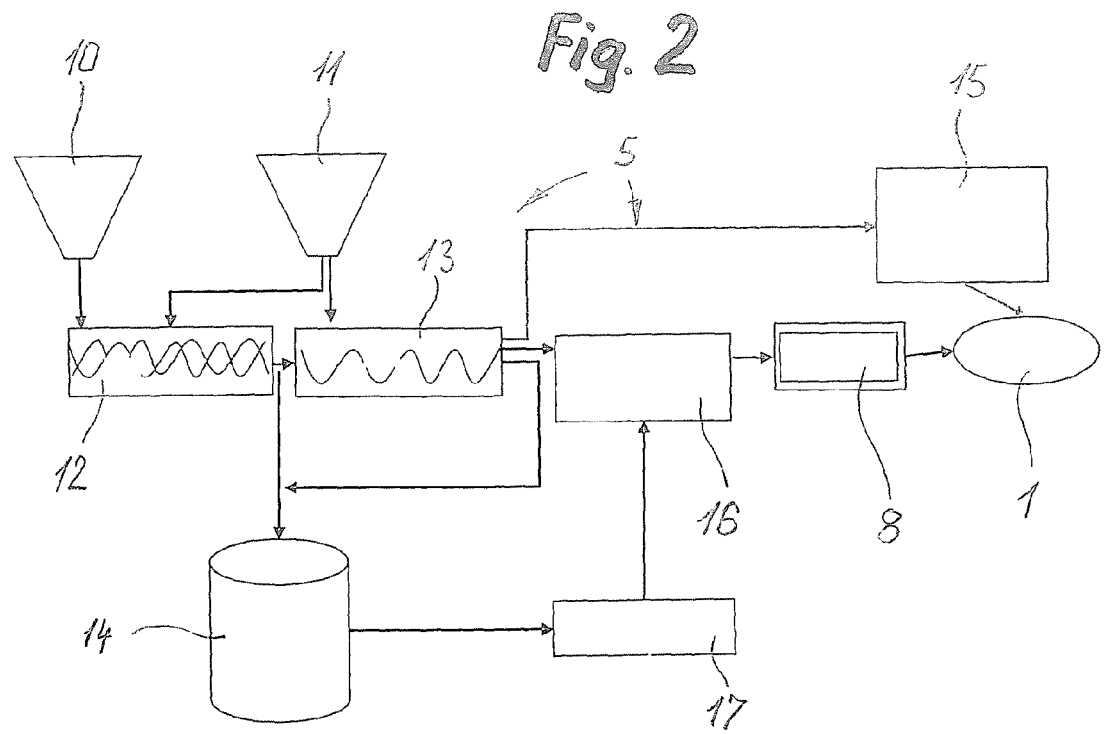
Figure 3:
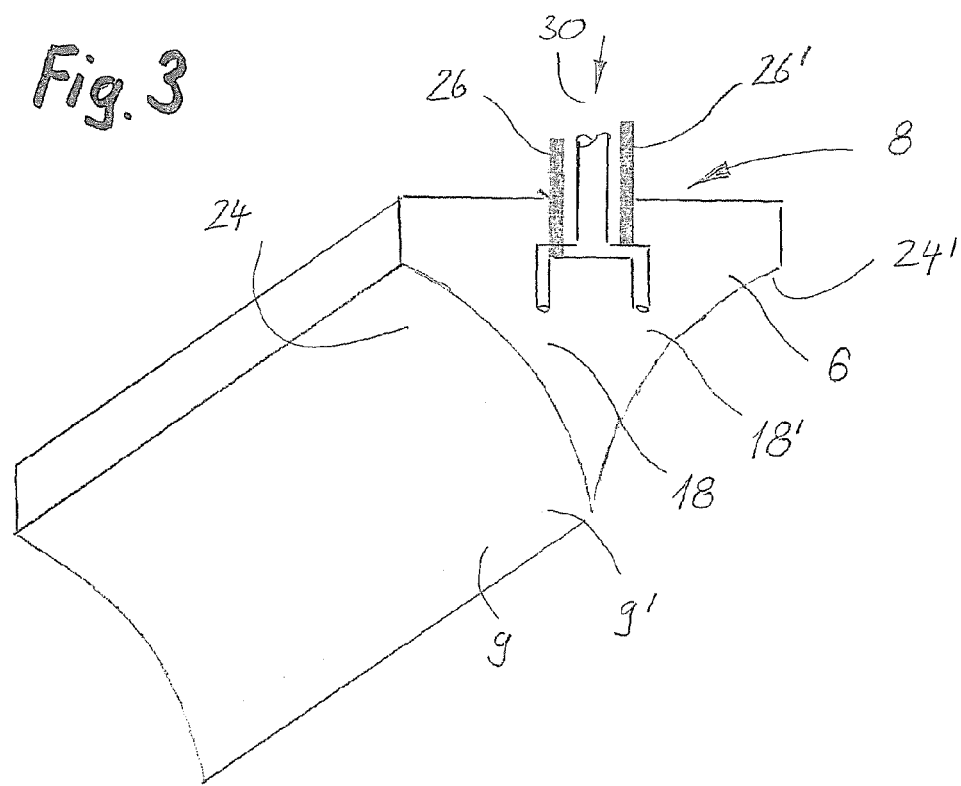
Figure 4:
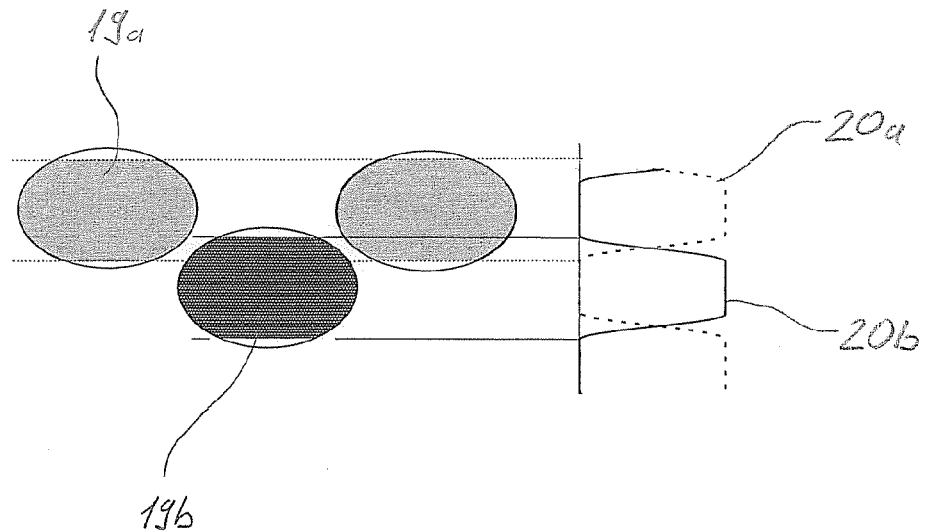
Figure 5:
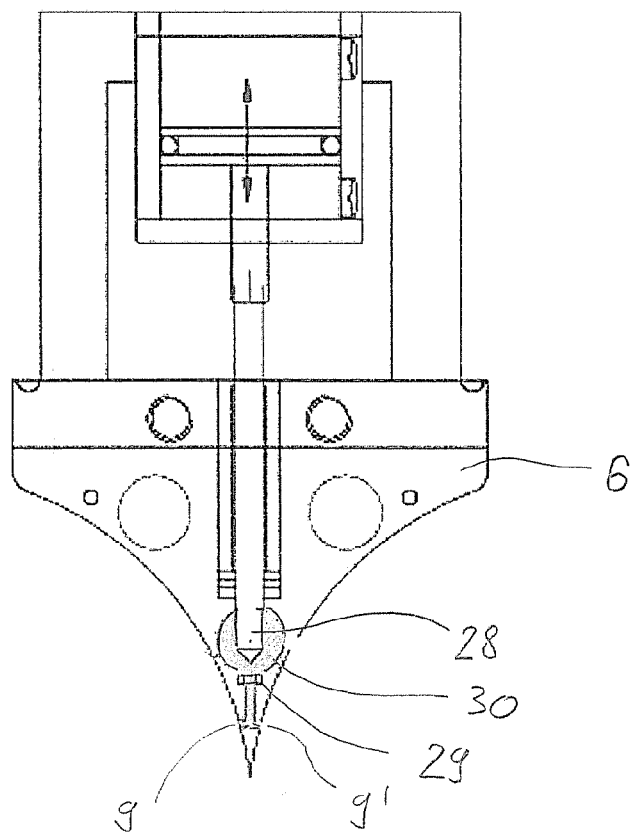
Figure 6A:
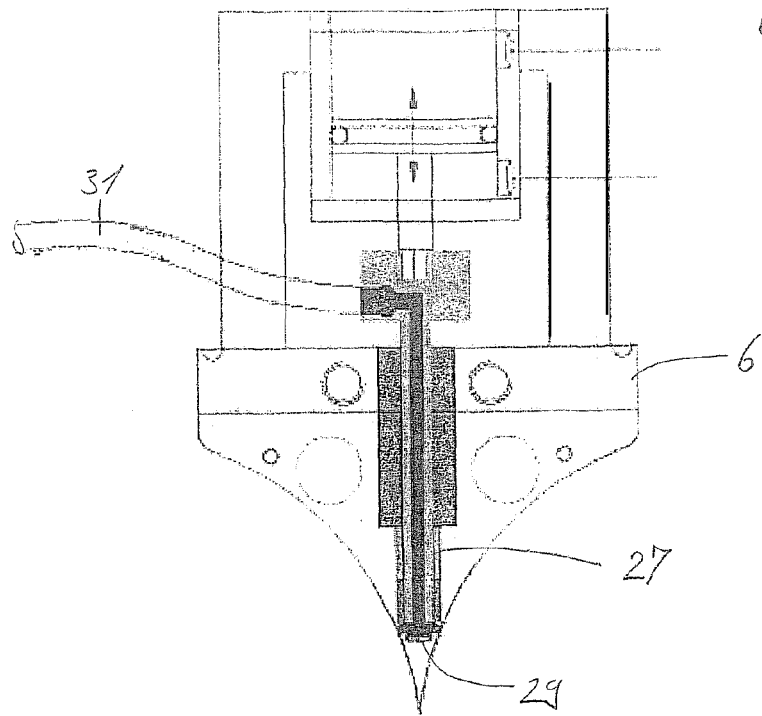
Figure 6B:
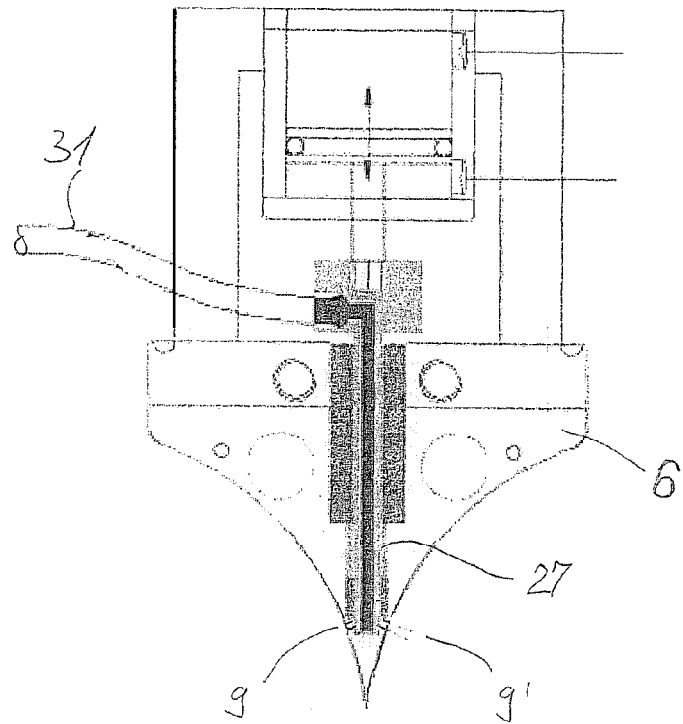
Figure 7:
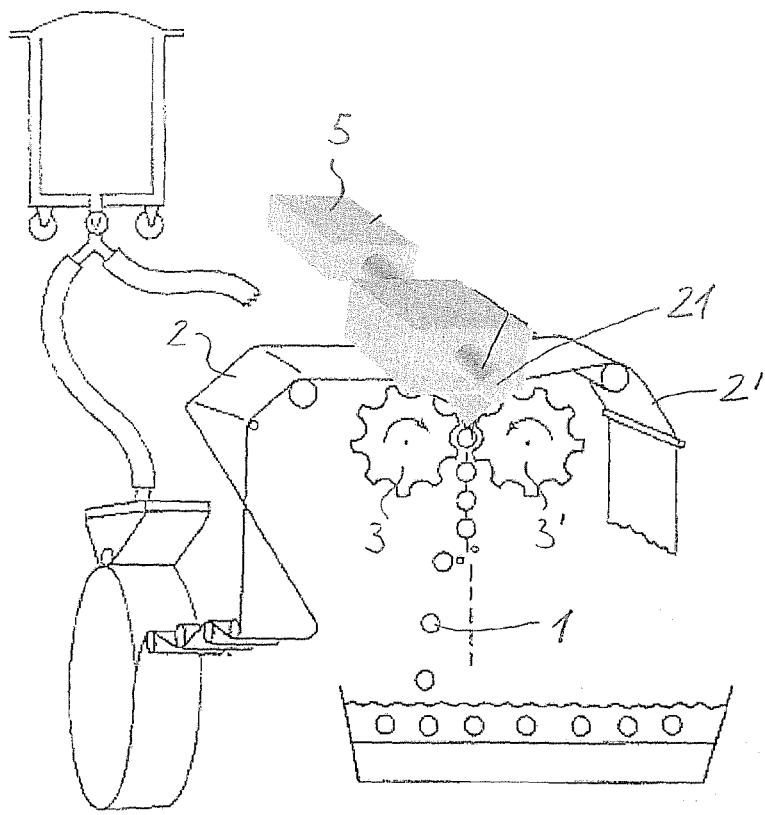
Figure 8:
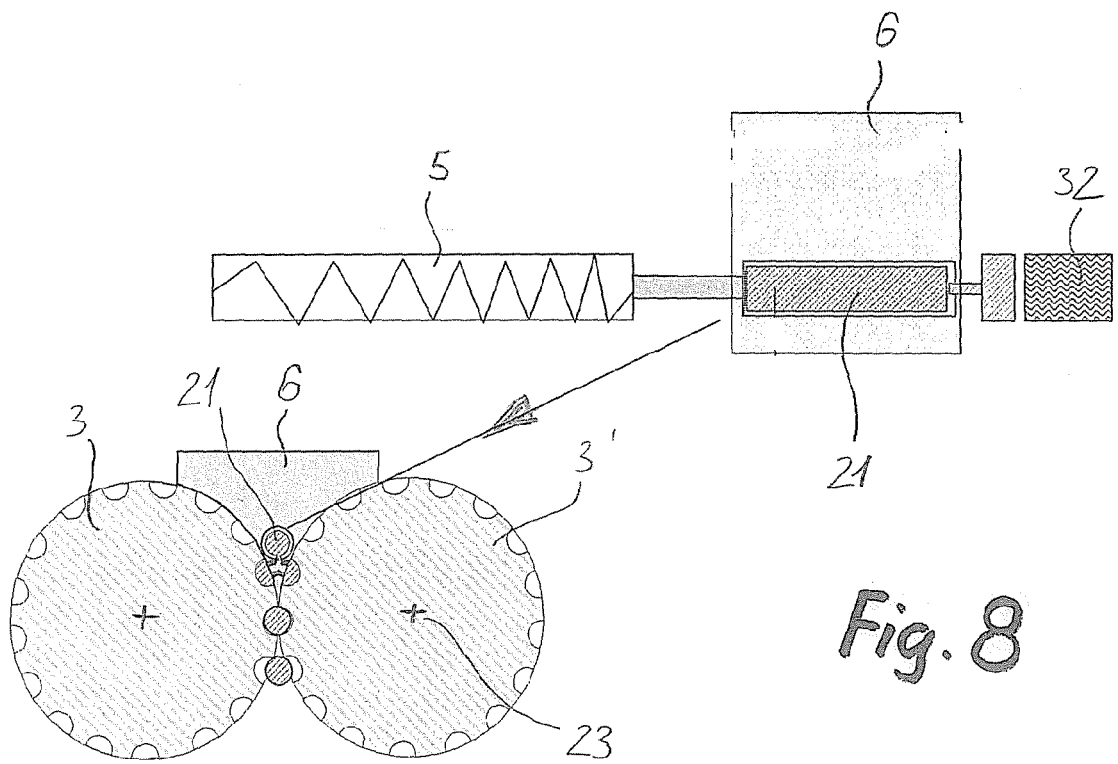
Figure 9:
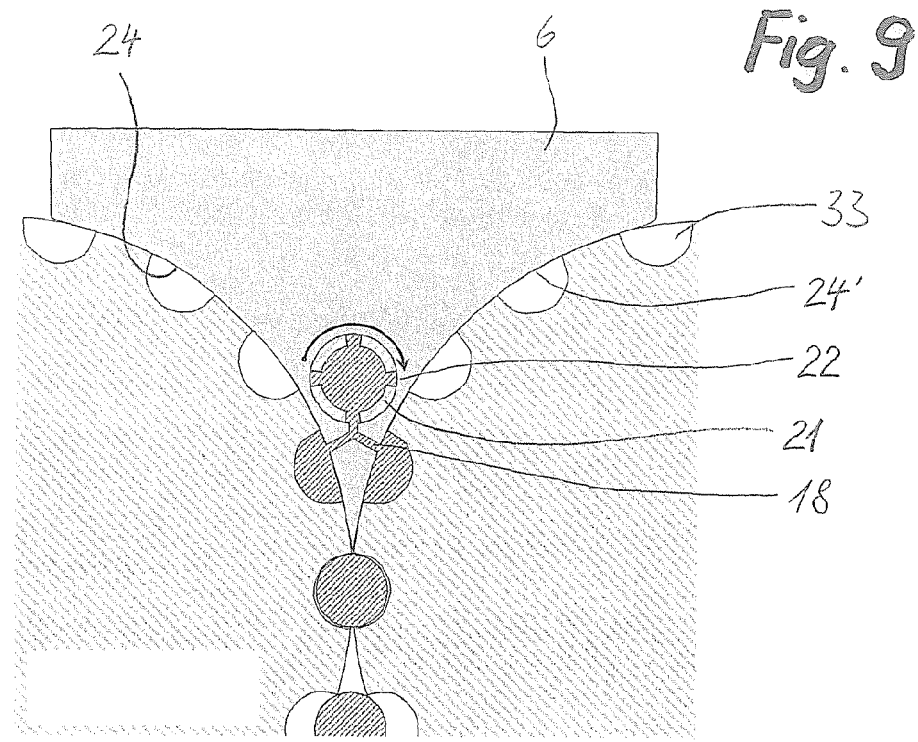
Figure 10:
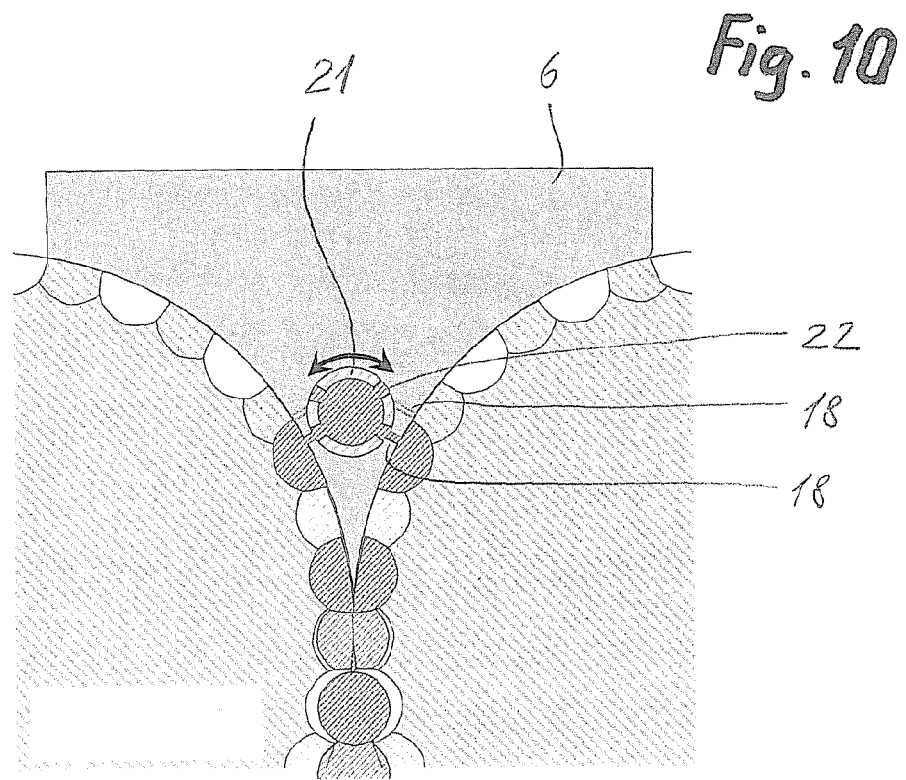
Figure 11:
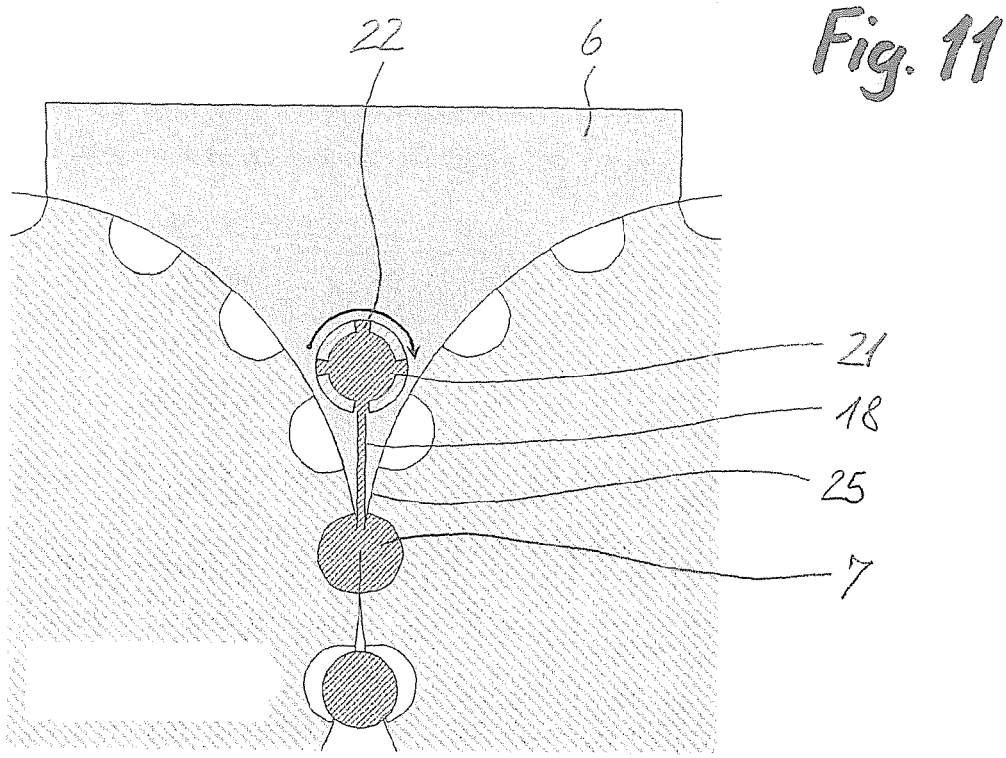
Figure 12:
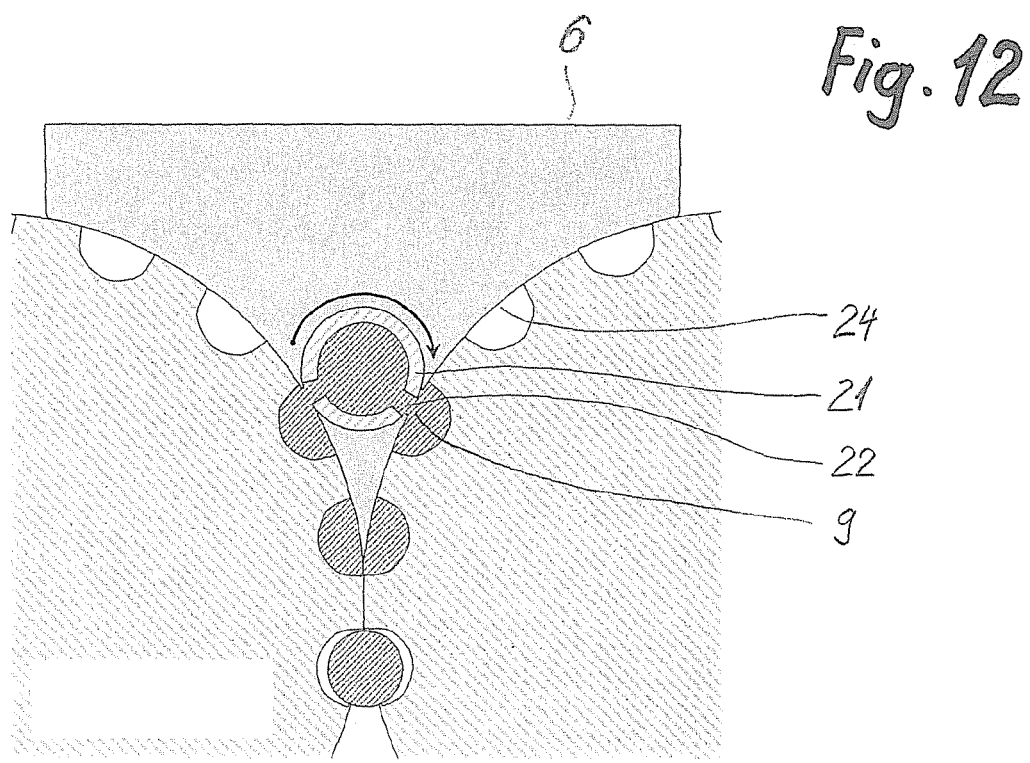

FIG. 2 shows a schematic representation of a rotary die installation according to the invention for processing viscous melt, FIG. 3 shows a perspective representation of a filling wedge with an installed portioner, FIG. 4 shows a schematic representation of the control of a portioner, FIG. 5 shows a greatly simplified representation of a portioner with valve needles, FIGS. 6a and 6b show greatly simplified representations of a portioner with a dosing tube in the opening and closing positions, FIG. 7 shows a schematic representation of a rotary die device with a portioner formed as a dosing hollow shaft, FIG. 8 shows the device according to FIG. 7 with further details, FIG. 9 shows a cross section through a filling wedge with a Y-shaped distributing channel and a permanently rotating dosing hollow shaft, FIG. 10 shows a cross section through a filling wedge with distributing channels leading directly to the wedge walls and an oscillating dosing hollow shaft, FIG. 11 shows a cross section through a filling wedge with a distributing channel to the wedge tip, and FIG. 12 shows a cross section through a filling wedge with discharge openings of the dosing hollow shaft directly adjoining the wedge surface.

Figure 1:
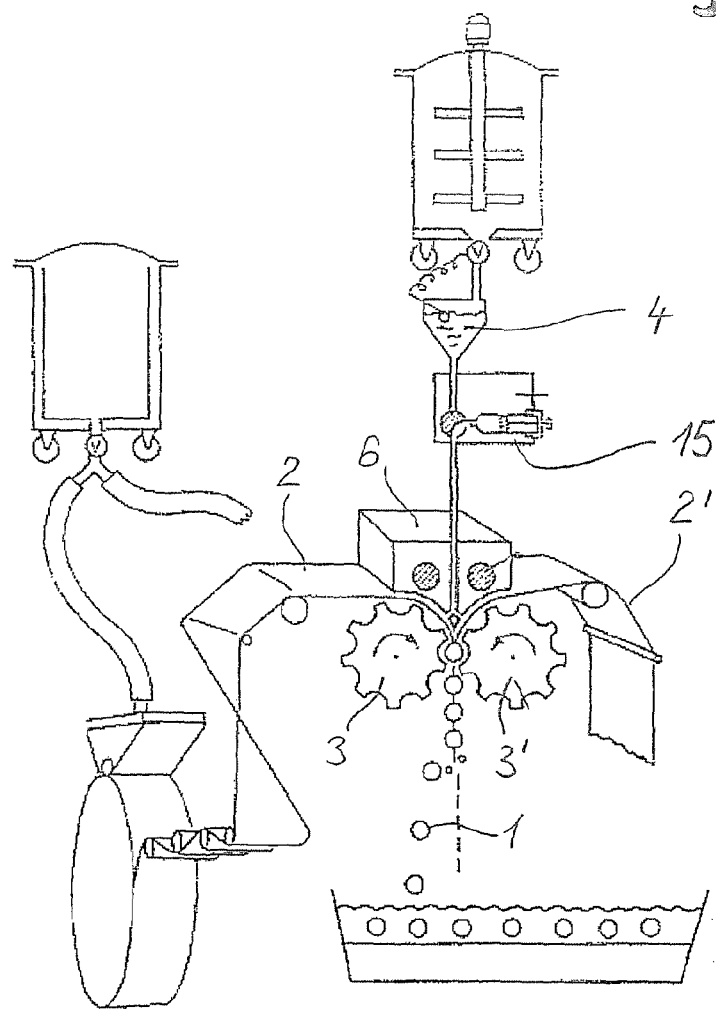
FIG. 1 shows a conventional rotary die device.
Figure 1A:
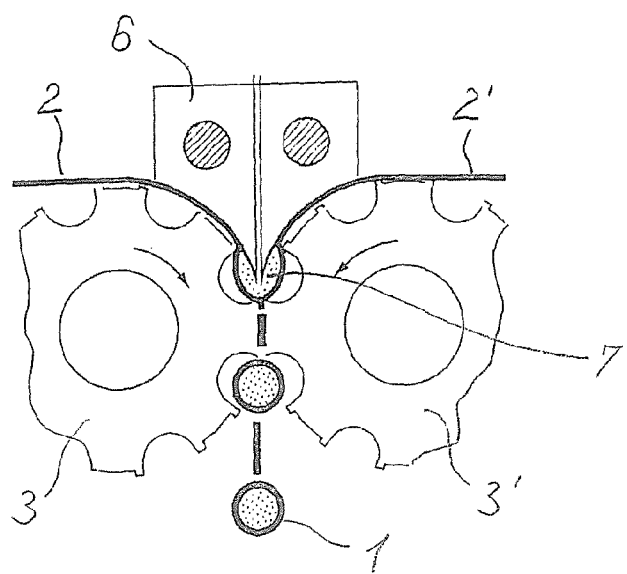
FIG. 1a shows a detail of the device according to FIG. 1.

FIG. 1 shows a conventional rotary die device with a conventional piston-type dosing pump 15 as a delivery means for the filling material 4. The filling material is brought by means of the piston-type dosing pump to the filling wedge 6, under which two endless bands of film 2, 2', for example of gelatin solution, are brought together on the two forming rolls 3, 3' and formed into capsules. Before the closing and pinching off of the capsules 1, the filling material is introduced into the capsule cavity 7 (FIG. 1a). The piston-type dosing pump 15 is arranged at a distance from the filling wedge 6 and it doses in a cyclical manner a volume corresponding to the desired degree of filling of the capsule. The dosed filling material must in this case overcome a distance of about 50 cm before it reaches the actual capsule filling location. Furthermore, the filling material covers this distance as a column which is advanced in a cyclical manner, which, as described at the beginning, in the case of high-viscosity liquids at high temperatures has adverse effects on the stability behavior, the dosing rate and the dosing accuracy, and affects the required pressure and mechanical stability of the structural components.

In FIG. 2, an overall installation for a rotary die process according to the invention is schematically represented. In a conventional dosing and mixing device 10, the powder or liquid components of the inactive matrix are prepared and homogeneously prepared in a melting and mixing installation 12 (such as for example a twin-screw extruder). The API may likewise be added at this stage by means of a mixer or doser.

The product created may be formed, cut, cooled and intermediately stored in an intermediate store 14, from where it can again be prepared into a melt in a later phase by a conventional mixing/melting device 13 (for example a single- or twin-screw extruder) or a melt-on-demand installation 17. The remelting of such filling material compositions with the aid of a melt-on-demand system 17, as commercially available for example from Robatech, Muri, Switzerland or ITW Dynatec, 31 Volunteer Drive, Hendersonville, Tenn., USA, is logistically particularly advantageous.

Alternatively, the solid matrix without API from the intermediate store 14 may be melted in the melting/mixing installation 13 and API kneaded in, for example in a crystalline or generally particulate form from the mixer/doser 11, and processed into a homogeneous melt or else into a molten suspension. A person skilled in the art can choose the structural design of the extruders and their operating conditions to correspond to the desired application conditions. It can thus also be ensured that the crystallinity of the API is retained. Particularly preferably, the active substance is added to the melt in a controlled grain size or microparticulate form (micronized, pelletized or coated).

The desired, viscous material obtained at the end of 13 or 17 is dosed into the capsule 1 directly by means of a conventional dosing pump 15 or alternatively dosed into the capsule 1 by means of a melt pump 16, by way of the doser 8. In a particularly preferred embodiment, a melt pump 16 with a differential pressure controller is arranged downstream of one or more extruders or melt-on-demand systems. This ensures that no pressure fluctuations occur, whereby a decidedly uniform stream can be achieved. Such melt pumps are commercially available, for example from Harrel Inc., East Norwalk, Conn., USA. Suitable melt pumps are also available, however, from Robatech, Muri, Switzerland, or other manufacturers of machines in the plastics industry.

A person skilled in the art will choose from the variants presented an optimum process for the set object of exact dosing. In principle, all the devices known from the plastics or hotmelt adhesives industry are available for this.

In the case of the installation according to FIG. 2, it can be seen that both the extruders 12 and 13 and the melt pump 16 may perform the function of a delivery means, generally denoted by 5, to deliver to the portioner 8 a stream of material that is as uniform and free from pressure fluctuations as possible. Delivery devices which operate on the reciprocating displacement principle, such as for example piston-type pumps, are not suitable for this. A conventional piston-type dosing pump 15, however, may nevertheless be integrated in the system, in order to process the filling material in a conventional way, and without a portioner 8, into capsules 1 for rapid melting and mixing operations and low-viscosity compositions.

FIG. 3 schematically shows a filling wedge 6, in which the portioner 8 is formed as a double slide with the two vertically movable slide elements 26, 26'. In this case, a central feed line 30 is divided into separate distributing channels 18, 18', it being possible for these distributing channels to be alternately opened and closed by the slide elements 26, 26'. The distributing channels 18, 18' lead to filling material outlet openings 9, 9' on the two opposing wedge surfaces 24, 24'. At the central feed line 30, the melt is fed in under constant pressure.

The opening times and the opening cross sections at the slide elements are chosen such that the volumetric flow under constant pressure is proportional to the dosed amount that flows into the capsule through the outlet openings 9. In order not to produce any pressure fluctuations and in order to cut slowly through the viscous volumetric flow, the respectively released opening cross sections of successively filled capsules follow an approximately sinusoidal, specifically sinusoidally superposed, profile. This situation is schematically represented in FIG. 4. The opening cross sections 19a, 19b are superposed, producing two opposing and likewise superposed sine curves 20a, 20b. The amplitude of this curve respectively corresponds to the cross section that is released as a maximum. As can be seen, with such control, the opening cross section of one row is continuously reduced while the opening cross section of the following row is already being opened. Such control of the slide elements may be performed, for example, by means of a camshaft.

FIG. 5 shows an exemplary embodiment of a filling wedge 6, in which the portioner has a number of valve needles 28 corresponding to the number of capsules to be filled, which needles are cyclically operated and interact with corresponding valve seats 29. The valve needles are mounted over the filling wedge and move in a perpendicular direction in the axis of symmetry of the filling wedge. The central feed line 30 delivers the melt under uniform pressure at right angles to the valve needles. From the valve seat 29, a central distributing channel leads to the outlet openings 9, 9'(Y channel). The valve needles are also preferably opened and closed in a manner corresponding to a sine curve and, for example, are actuated by means of a camshaft or by means of electronically controlled pneumatics or hydraulics.

In FIGS. 6a, 6b, a further exemplary embodiment of a portioner, which operates on the slide principle, is represented. Instead of the valve needles, a number of dosing tubes 27 which can be activated in the same way or a similar way are mounted in a row in the filling wedge. The melt coming from the delivery means is introduced into the dosing tubes, for example, by way of flexible lines 31. In a cyclical manner, the lower free end of each dosing tube is pressed against the valve seat 29 and thereby closed, as represented in FIG. 6a. As soon as the tube is raised, filling material flows by way of very short channels to the filling material openings 9, 9'. The opening position is represented in FIG. 6b.

In the case of the exemplary embodiment according to FIGS. 7 and 8, the portioner comprises a dosing hollow shaft 21, which is mounted rotatably in the filling wedge parallel to the axes of rotation 23 of the forming rolls 3, 3'. As described more precisely below, this dosing hollow shaft is provided on its lateral surface with discharge openings and is in direct connection with the delivery means 16, 13 or 17 for the melt to be fed in free from pressure fluctuations. For example by means of an electric motor 32, the dosing hollow shaft 21 may be moved continuously in the same rotational sense or in an oscillating manner in both directions of rotation. The drive motor is in this case arranged on the side facing away from the feed line for the melt. For the connection to the delivery means 5, corresponding rotating mechanical seals are required, to make the rotational movement possible.

A first exemplary embodiment of a dosing hollow shaft 21 is represented in FIG. 9. The dosing hollow shaft conducting the filling material is provided with four discharge openings 22 arranged with a regular angular division. With the dosing hollow shaft 21 rotating in the same sense, these openings respectively correspond in one angular position to a distributing channel 18, which leads in a Y-shaped manner to separate outlet openings, which lie at the same height and each fill a capsule half. By the choice of opening angle or slot, the right rotational speed, and consequently the dwell time or passing time of the discharge openings 22 over the distributing channels 18, the composition is portioned in a manner dependent on the viscosity and the pressure. The diameter of the distributing channels 18 is in this case at least 1 mm, but preferably at least 2 mm and still more preferably one third of the capsule diameter or one third of the width of a cup 33 in the forming roll running past the filling hole. For reasons of overall clarity, the band of film between the forming rolls and the filling wedge is not represented in the exemplary embodiments described and following hereafter.

A further exemplary embodiment of a dosing hollow shaft 21 is represented in FIG. 10. In this case, two separate rows of distributing channels 18 are arranged on each side of the filling wedge, each of which rows leads to a separate, laterally offset cup on the forming roll. The discharge openings 22 are not arranged with a uniform angular division, but together in pairs, and the dosing hollow shaft 21 does not move in the same sense but in an oscillating manner in both directions of rotation. In this case, the individual distributing channels are released in alternation.

In the case of the exemplary embodiment according to FIG. 11, the dosing hollow shaft 21 is driven in the same way and constructed in the same way as in the case of the exemplary embodiment according to FIG. 9. However, a single distributing channel 18 leads directly at the wedge tip 25 into the developing capsule cavity 7. This is known as buttonhole filling. It goes without saying that, instead of a continuous movement, the dosing hollow shaft could likewise be oscillated in both directions of rotation.

Finally, FIG. 12 shows another exemplary embodiment, in which the distributing channels are in fact omitted entirely. The discharge openings 22 on the dosing hollow shaft 21 coincide virtually with the filling material outlet openings 9 in the wedge surfaces 24 of the filling wedge. In the case of this solution, it is not possible for the dosing hollow shaft 21 to have the same outside diameter throughout, because if that were the case the wedge tip could not be connected to the rest of the filling wedge with sufficient mechanical stability. On the other hand, screwing of the filling wedge tip to the filling wedge body can be achieved by narrowing the dosing shaft between the dosing points.

According to the invention, the capsule is preferably shock-cooled after production, in order to make the filling material glassy. This is preferably performed by cold gases (nitrogen, air, $CO_2$) or by a cold bath of liquids that are compatible with the enclosing shell.

The soft capsules according to the invention can be used for all conventional purposes for which soft capsules are used. Oral, rectal or vaginal application may be mentioned by way of example, it being possible for the capsule to be applied as a food supplement, pharmaceutical product, medical product or for cosmetic or technical purposes.

The invention claimed is:

1. A device for producing soft capsules on the rotary die principle, with two forming rolls, which can be driven counter to each other and between which two bands of film which can be continuously fed in can be formed into capsules, with a filling wedge arranged in the intake region of the forming rolls, for feeding a liquid filling material into the forming capsule cavity, and with a delivery means for pressurizing the filling material, wherein with the delivery means, at least one continuous stream of filling material can be produced, and in that the stream of filling material can be divided into individual portions by a portioner arranged separately from the delivery means, which portions can be fed to the capsule filling location.

2. The device according to claim 1, wherein with the delivery means said at least one continuous stream of filling material can be produced free from pressure fluctuations.

3. The device according to claim 1, wherein said portioner is arranged within the filling wedge.

4. The device according to claim 1, wherein the delivery means is a circulatory displacement delivery means.

5. The device according to claim 4, wherein said circulatory displacement delivery means is a screw pump.

6. The device according to claim 4, wherein said circulatory displacement delivery means is a melt extrusion device.

7. The device according to claim 1, wherein distributing channels with a maximum length of 50 mm are arranged on the surfaces of the filling wedge between the portioner and the capsule filling location.

8. The device according to claim 1, wherein distributing channels with a maximum length of 30 mm are arranged on the surfaces of the filling wedge between the portioner and the capsule filling location.

9. The device according to claim 1, wherein the stream of filling material can be divided at the portioner into at least two partial streams, which can be directed to separate filling locations directly or by way of separate distributing channels, it being possible for the partial streams to be achieved phase-shifted one after the other.

10. The device according to claim 1, wherein, for feeding the two partial streams at the portioner, opening cross sections for each partial stream can be exposed and closed again one after the other on the basis of sinusoidally superposed curves.

11. The device according to claim 1, wherein the portioner has at least one dosing hollow shaft, which is rotatably mounted in the filling wedge and has discharge openings, which in at least one rotary angle position coincide with an opening or with a channel in the filling wedge.

12. The device according to claim 1, wherein the dosing hollow shaft is mounted parallel to the axes of rotation of the forming rolls and in that each discharge opening can be connected either to a channel leading to the wedge surfaces or to a channel leading to the wedge tip of the filling wedge.

13. The device according to claim 1, wherein the portioner has at least one dosing slide, which is mounted linearly displaceably in the filling wedge and with which feed channels for the filling material can be exposed and closed in a cyclical manner.

14. The device according to claim 1, wherein the dosing slide is mounted perpendicularly to a plane running through the two axes of rotation of the forming rolls.

15. The device according to claim 1, wherein the dosing slide is formed as a dosing tube by way of which the filling material can be fed.

16. The device according to claim 1, wherein the portioner has at least one valve needle, which interacts with a valve seat in the filling wedge.

* * * * *